United States Patent
Zhang et al.

(10) Patent No.: US 12,397,287 B1
(45) Date of Patent: Aug. 26, 2025

(54) PRETREATMENT PROCESS OF RESIN CATALYST FOR SYNTHESIZING BISPHENOL A

(71) Applicant: TIANJIN UNIVERSITY, Tianjin (CN)

(72) Inventors: Minhua Zhang, Tianjin (CN); He Dong, Tianjin (CN); Hao Gong, Tianjin (CN); Guochao Yang, Tianjin (CN); Yingzhe Yu, Tianjin (CN)

(73) Assignee: Tianjin University, Tianjin (CN)

( * ) Notice: Subject to any disclaimer, the term of this patent is extended or adjusted under 35 U.S.C. 154(b) by 0 days.

(21) Appl. No.: 18/973,915

(22) Filed: Dec. 9, 2024

(30) Foreign Application Priority Data

Apr. 22, 2024 (CN) .......................... 202410481158.9

(51) Int. Cl.
| | | |
|---|---|---|
| *B01J 38/04* | (2006.01) | |
| *B01J 19/00* | (2006.01) | |
| *B01J 31/08* | (2006.01) | |
| *B01J 35/45* | (2024.01) | |
| *B01J 38/52* | (2006.01) | |

(52) U.S. Cl.
CPC ........... *B01J 38/04* (2013.01); *B01J 19/0013* (2013.01); *B01J 31/08* (2013.01); *B01J 35/45* (2024.01); *B01J 38/52* (2013.01); *B01J 2219/00051* (2013.01)

(58) Field of Classification Search
CPC ........ B01J 38/04; B01J 35/45; B01J 19/0013; B01J 31/08; B01J 38/52; B01J 2219/00051; B01J 41/08; B01J 38/48
USPC ........................................ 502/12, 22, 29, 34
See application file for complete search history.

(56) References Cited

U.S. PATENT DOCUMENTS

| | | | | |
|---|---|---|---|---|
| 3,634,341 A | * | 1/1972 | Gammill | C07C 37/20 521/30 |
| 3,760,006 A | * | 9/1973 | Gammill | B01J 31/10 568/728 |
| 5,146,007 A | | 9/1992 | Cipullo | |
| 5,723,691 A | * | 3/1998 | Cipullo | C07C 37/20 568/723 |

(Continued)

FOREIGN PATENT DOCUMENTS

| | | |
|---|---|---|
| DE | 2164339 A1 | 6/1973 |
| FR | 1218070 A | 5/1960 |

OTHER PUBLICATIONS

Jie Xu et al. "Biobased novolac resins cured with DGEBA using water-insoluble fraction of pyrolysis bio-oil: Synthesis and characterization", Journal of the Taiwan Institute of Chemical Engineers, Jul. 26, 2022.

(Continued)

*Primary Examiner* — Patricia L. Hailey

(57) ABSTRACT

There is provided a pretreatment process for a resin catalyst for synthesizing bisphenol A. The pretreatment process includes the following steps: firstly, purging the resin catalyst with gas, to remove residual liquid in the resin catalyst; secondly, allowing the vented resin catalyst to be in contact with a replacement washing solution for static replacement, and removing the replacement washing solution; thirdly, allowing the obtained resin catalyst to be in contact with a replacement washing solution for static replacement; and finally, allowing a leachate to be in contact with the resin catalyst, and removing the leachate, to obtain a pretreated resin catalyst.

10 Claims, 1 Drawing Sheet

(56) References Cited

U.S. PATENT DOCUMENTS

2003/0017935 A1* 1/2003 Peemans .............. B01J 31/4007
502/29

OTHER PUBLICATIONS

Jinlai Qin et al. "Catalysts for Synthesis of Bisphenol A", Jul. 30, 2004.
Wei-Li Xu et al. "Synthesis and properties of phenol amine aldehyde resin demulsifiers" Jan. 20, 2015.

* cited by examiner

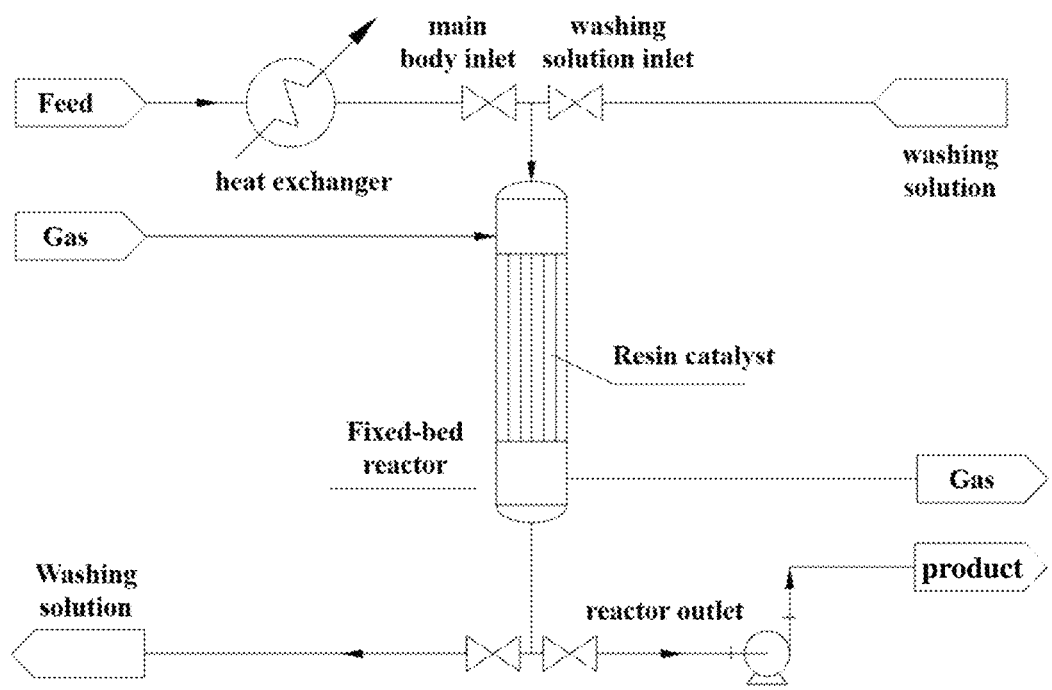

PRETREATMENT PROCESS OF RESIN CATALYST FOR SYNTHESIZING BISPHENOL A

CROSS-REFERENCE TO RELATED APPLICATION

This application claims priority from the Chinese patent application 202410481158.9 filed Apr. 22, 2024, the content of which is incorporated herein in the entirety by reference.

TECHNICAL FIELD

The present disclosure relates to a resin catalyst pretreatment process for catalytically synthesizing bisphenol A by a resin catalyst, in particular to a process for reducing a water content in a resin catalyst for catalyzing bisphenol A.

BACKGROUND ART

Bisphenol A (BPA), with a chemical name of 2,2-bis(4-hydroxyphenyl)propane, is a widely-used organic chemical raw material prepared through condensation between phenol and acetone under an action of a catalyst, which is mainly used for producing various high polymer materials such as polycarbonate and epoxy resin.

A process for synthesizing bisphenol A by using an ion exchange resin method has advantages such as simple in flow, less corrosive to equipment and fewer in emissions of "three wastes" (industrial wastewater, waste gases, and residues), and has been widely used industrially. The catalyst used in this method is ion exchange resin obtained after sulfonation or sulfydryl modification with styrene or substituted styrene as a monomer, divinyl benzene and the like as a crosslinking agent, and liquid paraffin and the like as a pore-forming agent, featuring high catalytic activity and good selectivity. Although the ion exchange resin catalyst has a smooth pore structure and an appropriate acid amount and pH value, the residual synthesis monomer, crosslinking agent and pore-forming agent during preparation of the resin will lead to side reactions, or even pore blockage, thereby affecting catalytic performance. In addition, residual water in the ion exchange resin will lead to a reverse shift in the equilibrium of a bisphenol A synthesis reaction, reducing a conversion rate of the synthesis reaction; and meanwhile, the water will occupy an active center of the catalyst, resulting in a decrease in catalytic activity, thereby reducing a reaction rate. Thus, it is necessary to pretreat the ion exchange resin before use, so as to remove residues and water from resin synthesis.

CN100546963C has invented a commercial scale continuous process for the production of a bisphenol comprising reacting a phenol and a ketone. The ketone and the phenol are directly in contact and reaction with modified ion exchange resin catalyst, to obtain the bisphenol in this method. CN1150150C has invented a method for preparing bisphenol A, which comprises reacting phenol with acetone in the presence of an acid ion-exchange resin as a catalyst and an alkyl mercaptan as a cocatalyst, to obtain the bisphenol A in this reaction process. CN103974925B has invented a method for the preparation of the dihydric phenol 2,2 bis (4'-hydroxyphenyl) propane. An antioxidant and an ion exchange resin catalyst are in contact before phenol and acetone react with the catalyst, to form a treated and promoted catalyst in this process, such that stability and catalytic reaction performance of the catalyst are improved. However, no method or standard requirement for reducing a water content and activation during resin pretreatment is involved in reports of these methods for preparing the bisphenol A, while these factors are critical to affecting efficient catalytic synthesis of the bisphenol A by the resin catalyst and catalytic stability of the resin catalyst.

At present, a pretreatment method for a resin catalyst for catalytically synthesizing bisphenol A industrially is as follows: injecting reactant phenol as a washing solution into a fixed-bed reactor filled with the resin catalyst to be in contact with the resin catalyst, so as to replace or wash residues and water in resin. Although this method can remove the residues and the water from the resin, it is long in operation time, large in consumption of the phenol washing solution and high in pretreatment cost, and a water content of the resin can hardly be reduced to below 1.0 wt %.

In conclusion, in an existing reaction process for catalytically synthesizing the bisphenol A by the resin catalyst, no pretreatment process for the resin catalyst is considered, and especially, no strict definitive standard and effective resin pretreatment operation solution are available for controlling the water content in the resin catalyst before reaction. Thus, it is necessary to develop a resin catalyst pretreatment process for catalytically synthesizing the bisphenol A by the resin catalyst, so as to shorten time of the pretreatment process, and reduce a washing solution consumption during pretreatment, thereby reducing a water content in the resin catalyst rapidly to below 1.0 wt %.

Thus, the present disclosure develops a new pretreatment method for the resin catalyst and an appropriate phenol concentration and phenol consumption matched therewith in order to solve the problems that treatment time is long, the phenol consumption is large, and the water content in the resin catalyst is not easy to control in the pretreatment process for the resin catalyst for catalyzing the bisphenol A. The main innovation lies in that a continuous treatment method of purging for emptying, static replacement, and washing is proposed, and resin catalyst is subjected to static replacement and washing with phenol aqueous solutions at different concentration gradients, to drain physically bound water (bound water) inside particles of the resin catalyst in a resin catalyst bed and water (non-bound water) highly bound to the resin catalyst and hardly desorbed.

SUMMARY OF THE DISCLOSURE

The present disclosure aims at providing a resin catalyst pretreatment process for catalytic synthesis of bisphenol A by a resin catalyst, adopts the steps of removing residual liquid in the resin catalyst, and then performing static replacement: the removed resin catalyst in a fixed-bed reactor is adopted as a replaced substance, the resin catalyst is in a static state relative to the reactor, and phenol, as a replacement solution, is in contact with the resin catalyst and enters a pore structure inside the replaced substance, to replace water inside pores of the replaced substance.

The vented resin catalyst is in contact with the replacement washing solution, the replacement washing solution is removed, the resin obtained after performing static replacement continues to be in contact with a replacement washing solution to perform static replacement, finally, a leachate is in contact with the resin catalyst in a leaching manner, and removing the leachate, to obtain a resin catalyst with a low water content. The water in the resin catalyst for catalytically synthesizing the bisphenol A can be rapidly and effectively removed through this process technology, resin pretreatment time is short, and the washing solution consumption is small.

In order to achieve the objectives of the present disclosure, the technical solution of the present disclosure is as follows:

A resin catalyst pretreatment process for catalytically synthesizing bisphenol A by a resin catalyst, includes the following steps:
(a) removing residual liquid from the resin catalyst; specifically, purging the resin catalyst with purging gas to remove the residual liquid in the resin catalyst;
(b) allowing the vented resin catalyst to be in contact with a replacement washing solution for static replacement, and removing the replacement washing solution;
(c) allowing the obtained resin catalyst to be in contact with a replacement washing solution for static replacement; and
(d) allowing a leachate to be in contact with the resin catalyst in a leaching manner, and removing the leachate, to obtain a pretreated resin catalyst; wherein
the replacement washing solutions in the above steps (c) and (b) are both phenol aqueous solutions, and the phenol concentration of phenol aqueous solution in step (c) is higher than that of the phenol aqueous solution in the step (b).

According to the resin catalyst pretreatment process for catalytically synthesizing the bisphenol A by the resin catalyst, the step (a) is specifically as follows: introducing the purging gas into a fixed-bed reactor from a gas inlet in an upper portion of the fixed-bed reactor to be in contact with the resin catalyst, removing liquid from the resin catalyst, to obtain the vented resin catalyst, and exhausting the purging gas from a gas outlet in a lower portion of the fixed-bed reactor;

the step (b) is specifically as follows: closing an outlet of the fixed-bed reactor, introducing the replacement washing solution into the fixed-bed reactor from a washing solution inlet to be in contact with the resin catalyst for static replacement, after completing static replacement, opening a washing solution outlet of the fixed-bed reactor, introducing the purging gas, and draining the washing solution from the outlet in a bottom of the fixed-bed reactor;

the step (c) is specifically as follows: closing the outlet of the fixed-bed reactor, and introducing the replacement washing solution into the fixed-bed reactor from the washing solution inlet to be in contact with the resin catalyst for static replacement; and the step (d) is as follows: introducing the leachate into the fixed-bed reactor from the washing solution inlet to be in contact with the resin catalyst for leaching, and opening the washing solution outlet of the fixed-bed reactor to drain the leachate, to obtain the pretreated resin catalyst.

In the above technical solution, the resin catalyst is acid ion exchange resin, which is one of a gel type or macroporous type, a resin crosslinking degree ranges from 1.0% to 20%, a particle size ranges from 0.4 nm to 5.0 nm, and a water content ranges from 20 wt % to 90 wt %.

In the above technical solution, in the step (a), the residual liquid in the resin catalyst is removed through purging of the purging gas, the purging gas enters from an upper portion of a resin catalyst bed, the residual liquid and tail gas are exhausted from a lower portion of the resin catalyst bed, and the purging gas is selected from one or a combination of air, ethane, propane, nitrogen, argon, and helium.

In the above technical solution, in the step (a), a temperature of the purging gas ranges from 40° C. to 80° C., a flow per minute of the purging gas is 1 to 5 times a filling volume of the resin catalyst, and purging time ranges from 10 minutes to 120 minutes.

In the above technical solution, in the step (b), during static replacement, a temperature of a resin catalyst bed ranges from 45° C. to 95° C., a phenol content of the replacement washing solution ranges from 10 wt % to 95 wt %, a temperature of the replacement washing solution ranges from 45° C. to 95° C., a consumption of the replacement washing solution is 0.5 to 3 times a filling volume of the resin catalyst, and standing time ranges from 0.5 hours to 24 hours.

In the above technical solution, in the step (b), the purging gas is one or a combination of air, ethane, propane, nitrogen, argon, and helium, a temperature of the purging gas ranges from 40° C. to 80° C., a flow per minute of the purging gas is 1 to 5 times a filling volume of the resin catalyst, and purging time ranges from 10 minutes to 120 minutes.

In the above technical solution, in the step (c), during static replacement, a temperature of a resin catalyst bed ranges from 45° C. to 95° C., a phenol content of the replacement washing solution ranges from 80 wt % to 99.5 wt %, a temperature of the replacement washing solution ranges from 45° C. to 95° C., a consumption of the replacement washing solution is 0.5 to 3 times a filling volume of the resin catalyst, and standing time ranges from 0.5 hours to 24 hours.

In the above technical solution, in the step (d), the leachate is phenol, and a temperature of the leachate ranges from 45° C. to 95° C.

In the above technical solution, in the step (d), a flow per hour of the leachate is 0.05 to 0.2 times a filling volume of the resin catalyst, and leaching time ranges from 0.5 hours to 72 hours.

The present disclosure aims at solving the following problems:

1. A new pretreatment method for the resin catalyst and an appropriate phenol concentration and phenol consumption matched therewith are developed in order to solve the problems of long treatment time, large phenol consumption, and difficult to control the water content in resin in the pretreatment process for the resin catalyst for catalyzing the bisphenol A. The main innovation lies in that a continuous treatment method of purging for emptying, static replacement, and washing is proposed, and the resin catalyst is subjected to static replacement and washing with phenol aqueous solutions at different concentration gradients.

2. Based on existing literature, no report on the pretreatment process for the resin catalyst is available in the process for catalyzing the bisphenol A by the resin catalyst. At present, usually the phenol, as a reaction material in a bisphenol A reaction is in contact with the resin catalyst before the reaction of catalytically synthesizing the bisphenol A by the resin, so as to remove the water from the resin catalyst. The present disclosure proposes the continuous treatment method of purging for emptying, static replacement, and washing for pretreatment dehydration on the resin catalyst.

3. A principle of the present disclosure is as follows: the continuous treatment method of purging for emptying, static replacement, and washing includes: ①. a process of purging for emptying, wherein in this process, water between the particles of the resin catalyst in the resin catalyst bed is drained; ②. a process of static replacement, wherein the phenol aqueous solution, as the replacement solution, enters the particles of the resin catalyst in the resin catalyst bed to drain the physically bound water (bound water) inside the particles of the resin catalyst in the resin catalyst bed under the action of replacement, and meanwhile, a dehydration rate is regulated and controlled to prevent the resin bed from excessive or rapid dehydration, which may lead to the shrinkage or even collapse of a porous structure inside the resin through a difference between the concentration gradients of the phenol aqueous solution in the replacement solution; and ③. a washing process, wherein in this process, the phenol in the washing solution enters the particles of the resin catalyst in the resin catalyst bed to remove water (non-bound water) that is less strongly bound to and hardly desorbed from the resin (the resin is formed by polymerized crosslinking of styrene and stilbene, wherein vinyl and phenyl are easy to highly interact with water) through a difference between concentrations of the phenol in the washing solution and the phenol in the resin catalyst. In conclusion, the present disclosure proposes the pretreatment process for the resin catalyst, which can sequentially remove the bound water and the non-bound water from the resin catalyst bed through the continuous treatment process of purging for emptying, static replacement, and washing and the difference between the concentration gradients of the washing solutions, and can rapidly reduce the water content in the resin catalyst at a low phenol consumption under the condition that the pore structure and chemical properties of the resin bed are unchanged.

The present disclosure has the following advantages and beneficial effects:

(1) the novel pretreatment process for resin catalyst for catalytically synthesizing the bisphenol A is characterized in that a pretreatment dehydration process for the resin catalyst is invented, which can rapidly remove the water in the resin catalyst for catalyzing synthesizing the bisphenol A, and pretreatment time of the resin catalyst is short.

(2) The novel pretreatment process for resin catalyst for catalytically synthesizing the bisphenol A is characterized in that the pretreatment dehydration process for the resin catalyst is invented, which can reduce the phenol consumption in the washing solution and reduce material consumption and energy consumption, such that the cost of the pretreatment cost is reduced.

(3) the novel pretreatment process for resin catalyst for catalytically synthesizing the bisphenol A is characterized in that a pretreatment dehydration process for the resin catalyst is invented, which can effectively remove the water from the resin catalyst for catalytically synthesizing the bisphenol A, such that the water content in the resin catalyst is less than 1.0 wt %.

BRIEF DESCRIPTION OF THE DRAWINGS

FIG. 1 is a simplified flowchart of a technical solution for pretreating a resin catalyst for catalytically synthesizing bisphenol A.

DETAILED DESCRIPTION OF THE EMBODIMENTS

The present disclosure is further described in detail below with reference to the accompanying drawings and specific examples. The following examples are merely descriptive and not restrictive, and do not limit the scope of protection of the present disclosure.

The specific implementation process of a method of the present application is described below with the specific examples.

Example 1

Step (a), 1 L of a gel type ion exchange resin catalyst was put in a fixed-bed reactor, wherein the resin catalyst has a crosslinking degree of 4%, a particle size ranges from 0.6 nm to 1.5 nm, and a water content of 60 wt %, a resin catalyst bed was preheated to 50° C., and was kept at 50° C. in the pretreatment process. An outlet valve on a lower portion of the fixed-bed reactor was opened, nitrogen (at a flow rate of 2 L/min) was introduced from an upper portion of the fixed-bed reactor, residual liquid in the gel type ion exchange resin catalyst was drained from an outlet in a bottom of the fixed-bed reactor, and the outlet valve on the lower portion of the fixed-bed reactor was closed after purging for 30 minutes.

Step (b), then 1.5 L of a phenol aqueous solution (10 wt % phenol content) was preheated to 50° C. and added into the fixed-bed reactor to be in contact with the resin catalyst, and the resin catalyst bed was kept at 50° C. for standing for 5 hours. The outlet valve on the lower portion of the fixed-bed reactor was opened, nitrogen (at a flow rate of 2 L/min) was introduced from the upper portion of the fixed-bed reactor, standing liquid was drained from the outlet in the bottom of the fixed-bed reactor, and the outlet valve on the lower portion of the fixed-bed reactor was closed after purging for 30 minutes.

Step (c), then 1.5 L of a phenol aqueous solution (99.5 wt % phenol content) was preheated to 50° C. and added into the fixed-bed reactor to be in contact with the resin catalyst, and the resin catalyst bed was kept at 50° C. for standing for 5 hours.

Step (d), the outlet valve on the lower portion of the fixed-bed reactor was opened, phenol (at a temperature of 50° C., and an addition amount of 0.05 L/h) was introduced from the upper portion of the fixed-bed reactor, a phenol washing solution was drained from the outlet in the bottom of the fixed-bed reactor, and leaching was performed for 24 hours, to obtain a pretreated resin catalyst.

According to the method in this example, pretreatment time of the resin catalyst was 35 hours, and a water content of the treated resin catalyst was reduced to 0.93 wt %, which met the pretreatment requirement that the water content of the resin catalyst is less than 1.0 wt %.

Example 2

Step (a), 1 L of a gel type ion exchange resin catalyst (a crosslinking degree of 8%, a particle size ranged from 0.4 nm to 1.5 nm, and a water content of 30 wt %) was put in a fixed-bed reactor, a resin catalyst bed was preheated to 70° C., and was kept at 70° C. in the pretreatment process. An outlet valve on a lower portion of the fixed-bed reactor was opened, air (at a flow rate of 2.5 L/min) was introduced from an upper portion of the fixed-bed reactor, residual liquid in the gel type ion exchange resin catalyst was drained from an outlet in a bottom of the fixed-bed reactor, and the outlet valve on the lower portion of the fixed-bed reactor was closed after purging for 60 minutes.

Step (b), then 1.5 L of a phenol aqueous solution (95 wt % phenol content) was preheated to 70° C. and added into the fixed-bed reactor to be in contact with the resin catalyst, and the resin catalyst bed was kept at 70° C. for standing for 4 hours. The outlet valve on the lower portion of the fixed-bed reactor was opened, air (at a flow rate of 2.5 L/min) was introduced from the upper portion of the fixed-bed reactor, standing liquid was drained from the outlet in the bottom of the fixed-bed reactor, and the outlet valve on the lower portion of the fixed-bed reactor was closed after purging for 60 minutes.

Step (c), then 1.5 L of a phenol aqueous solution (98.5 wt % phenol content) was preheated to 70° C. and added into the fixed-bed reactor to be in contact with the resin catalyst, and the resin catalyst bed was kept at 70° C. for standing for 4 hours.

Step (d), the outlet valve on the lower portion of the fixed-bed reactor was opened, phenol (at a temperature of 70° C., and an addition amount of 0.1 L/h) was introduced from the upper portion of the fixed-bed reactor, a phenol washing solution was drained from the outlet in the bottom of the fixed-bed reactor, and leaching was performed for 20 hours, to obtain a pretreated resin catalyst.

According to the method in this example, pretreatment time of the resin catalyst was 30 hours, and a water content of the treated resin catalyst was reduced to 0.95 wt %, which met the pretreatment requirement that the water content of the resin catalyst is less than 1.0 wt %.

Example 3

Step (a), 1 L of a macroporous ion exchange resin catalyst (a crosslinking degree of 6%, a particle size ranged from 0.8 nm to 2.0 nm, and a water content of 65 wt %) was put in a fixed-bed reactor, a resin catalyst bed was preheated to 45° C., and was kept at 45° C. in the pretreatment process. An outlet valve on a lower portion of the fixed-bed reactor was opened, argon (at a flow rate of 2 L/min) was introduced from an upper portion of the fixed-bed reactor, residual liquid in the macroporous ion exchange resin catalyst was drained from an outlet in a bottom of the fixed-bed reactor, and the outlet valve on the lower portion of the fixed-bed reactor was closed after purging for 30 minutes.

Step (b), then 2 L of a phenol aqueous solution (52.5 wt % phenol content) was preheated to 45° C. and added into the fixed-bed reactor to be in contact with the resin catalyst, and the resin catalyst bed was kept at 45° C. for standing for 4 hours. The outlet valve on the lower portion of the fixed-bed reactor was opened, argon (at a flow rate of 2 L/min) was introduced from the upper portion of the fixed-bed reactor, standing liquid was drained from the outlet in the bottom of the fixed-bed reactor, and the outlet valve on the lower portion of the fixed-bed reactor was closed after purging for 30 minutes.

Step (c), then 2 L of a phenol aqueous solution (80 wt % phenol content) was preheated to 45° C. and added into the fixed-bed reactor to be in contact with the resin catalyst, and the resin catalyst bed was kept at 45° C. for standing for 8 hours.

Step (d), the outlet valve on the lower portion of the fixed-bed reactor was opened, phenol (a temperature of 45° C., and an addition amount of 0.15 L/h) was introduced from the upper portion of the fixed-bed reactor, a phenol washing solution was drained from the outlet in the bottom of the fixed-bed reactor, and leaching was performed for 20 hours, to obtain a pretreated resin catalyst.

According to the method in this example, pretreatment time of the resin catalyst was 33 hours, and a water content of the treated resin catalyst was reduced to 0.92 wt %, which met the pretreatment requirement that the water content of the resin catalyst is less than 1.0 wt %.

Example 4

Step (a), 1 L of a macroporous ion exchange resin catalyst (a crosslinking degree of 10%, a particle size ranged from 0.5 nm to 1.2 nm, and a water content of 25 wt %) was put in a fixed-bed reactor, a resin catalyst bed was preheated to 90° C., and was kept at 90° C. in the pretreatment process. An outlet valve on a lower portion of the fixed-bed reactor was opened, nitrogen (at a flow rate of 1.5 L/min) was introduced from an upper portion of the fixed-bed reactor, residual liquid in the macroporous ion exchange resin catalyst was drained from an outlet in a bottom of the fixed-bed reactor, and the outlet valve on the lower portion of the fixed-bed reactor was closed after purging for 30 minutes.

Step (b), then 2.5 L of a phenol aqueous solution (75 wt % phenol content) was preheated to 90° C. and added into the fixed-bed reactor to be in contact with the resin catalyst, and the resin catalyst bed was kept at 90° C. for standing for 3 hours. The outlet valve on the lower portion of the fixed-bed reactor was opened, nitrogen (at a flow rate of 1.5 L/min) was introduced from the upper portion of the fixed-bed reactor, standing liquid was drained from the outlet in the bottom of the fixed-bed reactor, and the outlet valve on the lower portion of the fixed-bed reactor was closed after purging for 30 minutes.

Step (c), then 1.5 L of a phenol aqueous solution (90 wt % phenol content) was preheated to 90° C. and added into the fixed-bed reactor to be in contact with the resin catalyst, and the resin catalyst bed was kept at 90° C. for standing for 3 hours.

Step (d), the outlet valve on the lower portion of the fixed-bed reactor was opened, phenol (a temperature of 90° C., and an addition amount of 0.125 L/h) was introduced from the upper portion of the fixed-bed reactor, a phenol washing solution was drained from the outlet in the bottom of the fixed-bed reactor, and leaching was performed for 21 hours, to obtain a pretreated resin catalyst.

According to the method in this example, pretreatment time of the resin catalyst was 28 hours, and a water content of the treated resin catalyst was reduced to 0.90 wt %, which met the pretreatment requirement that the water content of the resin catalyst is less than 1.0 wt %.

Example 5

Step (a), 1 L of a gel type ion exchange resin catalyst (a crosslinking degree of 10%, a particle size ranged from 0.5 nm to 1.2 nm, and a water content of 27 wt %) was put in a fixed-bed reactor, a resin catalyst bed was preheated to 80° C., and was kept at 80° C. in the pretreatment process. An outlet valve on a lower portion of the fixed-bed reactor was opened, helium (at a flow rate of 2.5 L/min) was introduced from an upper portion of the fixed-bed reactor, residual liquid in the gel type ion exchange resin catalyst was drained from an outlet in a bottom of the fixed-bed reactor, and the outlet valve on the lower portion of the fixed-bed reactor was closed after purging for 60 minutes.

Step (b), then 2.0 L of a phenol aqueous solution (80 wt % phenol content) was preheated to 80° C. and added into the fixed-bed reactor to be in contact with the resin catalyst, and the resin catalyst bed was kept at 80° C. for standing for 4 hours. The outlet valve on the lower portion of the fixed-bed reactor was opened, helium (at a flow rate of 2.5 L/min) was introduced from the upper portion of the fixed-bed reactor, standing liquid was drained from the outlet in the bottom of the fixed-bed reactor, and the outlet valve on the lower portion of the fixed-bed reactor was closed after purging for 60 minutes.

Step (c), then 2.0 L of a phenol aqueous solution (95 wt % phenol content) was preheated to 80° C. and added into the fixed-bed reactor to be in contact with the resin catalyst, and the resin catalyst bed was kept at 80° C. for standing for 4 hours.

Step (d), the outlet valve on the lower portion of the fixed-bed reactor was opened, phenol (a temperature of 80° C., and an addition amount of 0.2 L/h) was introduced from the upper portion of the fixed-bed reactor, a phenol washing solution was drained from the outlet in the bottom of the fixed-bed reactor, and leaching was performed for 20 hours, to obtain a pretreated resin catalyst.

According to the method in this example, pretreatment time of the resin catalyst was 30 hours, and a water content of the treated resin catalyst was reduced to 0.98 wt %, which met the pretreatment requirement that the water content of the resin catalyst is less than 1.0 wt %.

Example 6

Step (a), 1 L of a gel type ion exchange resin catalyst (a crosslinking degree of 6%, a particle size ranged from 1.2 nm to 2.5 nm, and a water content of 40 wt %) was put in a fixed-bed reactor, a resin catalyst bed was preheated to 65° C., and was kept at 65° C. in the pretreatment process. An outlet valve on a lower portion of the fixed-bed reactor was opened, nitrogen (at a flow rate of 2.5 L/min) was introduced from an upper portion of the fixed-bed reactor, residual liquid in the gel type ion exchange resin catalyst was drained from an outlet in a bottom of the fixed-bed reactor, and the outlet valve on the lower portion of the fixed-bed reactor was closed after purging for 30 minutes.

Step (b), then 2.0 L of a phenol aqueous solution (70 wt % phenol content) was preheated to 65° C. and added into the fixed-bed reactor to be in contact with the resin catalyst, and the resin catalyst bed was kept at 65° C. for standing for 6 hours. The outlet valve on the lower portion of the fixed-bed reactor was opened, nitrogen (at a flow rate of 2.5 L/min) was introduced from the upper portion of the fixed-bed reactor, standing liquid was drained from the outlet in the bottom of the fixed-bed reactor, and the outlet valve on the lower portion of the fixed-bed reactor was closed after purging for 30 minutes.

Step (c), then 1.5 L of a phenol aqueous solution (90 wt % phenol content) was preheated to 65° C. and added into the fixed-bed reactor to be in contact with the resin catalyst, and the resin catalyst bed was kept at 65° C. for standing for 6 hours.

Step (d), the outlet valve on the lower portion of the fixed-bed reactor was opened, phenol (a temperature of 65° C., and an addition amount of 0.2 L/h) was introduced from the upper portion of the fixed-bed reactor, a phenol washing solution was drained from the outlet in the bottom of the fixed-bed reactor, and leaching was performed for 20 hours, to obtain a pretreated resin catalyst.

According to the method in this example, pretreatment time of the resin catalyst was 33 hours, and a water content of the treated resin catalyst was reduced to 0.96 wt %, which met the pretreatment requirement that the water content of the resin catalyst is less than 1.0 wt %.

Table 1 summarizes the examples of the present disclosure: resin catalyst water content before treatment, pretreatment time and resin catalyst water content after pretreatment. It can be shown from Table 1 that the pretreatment time of the pretreatment process for the resin catalyst in the present disclosure ranged from 28 hours to 35 hours under the condition that the resin catalyst water content after pretreatment was less than 1.0 wt %. It can be shown in conjunction with the examples of the present disclosure that the pretreatment process for the resin catalyst in the present disclosure has short pretreatment time and small washing solution consumption, and can rapidly and efficiently meet the requirement that the water content is less than 1.0 wt % during resin treatment.

TABLE 1

| Number | Resin catalyst water content (wt %) | Pretreatment time (hour) | Resin catalyst water content after pretreatment (wt %) |
|---|---|---|---|
| Example 1 | 60 | 35 | 0.93 |
| Example 2 | 30 | 30 | 0.95 |
| Example 3 | 65 | 33 | 0.92 |
| Example 4 | 25 | 28 | 0.90 |
| Example 5 | 27 | 30 | 0.98 |
| Example 6 | 40 | 33 | 0.96 |

The prior art and the examples of the present disclosure all adopt the phenol as the washing solution, the difference lies in that (1) in the prior art, only the phenol is used for washing the resin catalyst for dehydration, and this process is long in time and large in phenol consumption; (2) in the examples of the present disclosure, a continuous treatment method of purging for emptying, static replacement, and washing is used for pretreatment for dehydration on the resin catalyst, and specifically, water between particles of the resin catalyst in the resin catalyst bed is drained through purging for emptying in the present disclosure; during static replacement, the phenol aqueous solution, as a replacement solution, is used for draining physically bound water (bound water) inside the particles of the resin catalyst in the resin catalyst bed under the action of replacement; and in the washing process, water (non-bound water) that is less strongly bound to and hardly desorbed from the resin is removed by the phenol in the washing solution. In addition, the two methods differ in treatment condition, concentration of the washing solution and consumption of the washing solution.

In view of pretreatment effects, the method in the present disclosure can rapidly remove the water from the resin catalyst for catalytically synthesizing the bisphenol A, and the pretreatment time of the resin catalyst is short; the water in the resin catalyst for catalytically synthesizing the bisphenol A can be effectively removed, and the water content in the resin catalyst is less than 1.0 wt %; and the technical method has a good pretreatment effect for resin with different water contents, thereby achieving good adaptability. The water content in the resin catalyst obtained through the method in the present disclosure is greatly reduced to 1.0 wt %, which can meet the requirements for catalytic performance and stability of the resin that catalyzes acetone and phenol for the synthesis of the bisphenol A, while untreated resin catalyst will affect catalytic activity cannot meet industrial production requirements due to a high water content of 25 to 60 wt %, and especially, an increase in the water content leads to a decrease in a conversion rate of the phenol, a decrease in a yield of the bisphenol A and an increase in byproducts. The above description shows the technical necessity and advantages of the present disclosure.

The foregoing details of preferred implementations of the present disclosure have been described in conjunction with the accompanying drawings, however, the present disclosure is not limited to the specific details of the foregoing implementations, and various simple modifications may be made to the technical solution of the present disclosure within the scope of the technical concept of the present disclosure, where all the simple modifications fall within the scope of protection of the present disclosure.

In addition, it should be noted that various specific technical features described in the foregoing specific implementations can be combined in any appropriate manner without conflicts, and in order to avoid unnecessary repetitions, various possible combination manners are not additionally specified in the present disclosure.

In addition, various different implementations of the present disclosure can also be combined at will, and should also be regarded as the content disclosed in the present disclosure without departing from the thought of the present disclosure.

What is claimed is:

1. A pretreatment process of a resin catalyst for synthesizing bisphenol A, comprising the following steps:
   (a) removing residual liquid in the resin catalyst, specifically, purging the resin catalyst by using purge gas to remove the residual liquid in the resin catalyst and obtain a vented catalyst;
   (b) allowing the vented resin catalyst to be in contact with a replacement washing solution for static replacement, and removing the replacement washing solution;
   (c) allowing the obtained resin catalyst to be in contact with a replacement washing solution for static replacement; and
   (d) allowing a leachate to be in contact with the resin catalyst in a leaching manner, and removing the leachate, to obtain a pretreated resin catalyst; wherein the replacement washing solutions in step (c) and step (b) are both phenol aqueous solutions, and the phenol concentration of phenol aqueous solution in step (c) is higher than that of the phenol aqueous solution in the step (b).

2. The pretreatment process of the resin catalyst for synthesizing the bisphenol A according to claim 1, wherein the step (a) is specifically as follows: introducing the purging gas into a fixed-bed reactor from a gas inlet in an upper portion of the fixed-bed reactor to be in contact with the resin catalyst, removing liquid from the resin catalyst, to obtain the vented resin catalyst, and exhausting the purging gas from a gas outlet in a lower portion of the fixed-bed reactor;
the step (b) is specifically as follows: closing an outlet of the fixed-bed reactor, introducing the replacement washing solution into the fixed-bed reactor from a washing solution inlet to be in contact with the resin catalyst for static replacement, after completing static replacement, opening a washing solution outlet of the fixed-bed reactor, introducing the purging gas, and draining the washing solution from the outlet in a bottom of the fixed-bed reactor;
the step (c) is specifically as follows: closing the outlet of the fixed-bed reactor, and introducing the replacement washing solution into the fixed-bed reactor from the washing solution inlet to be in contact with the resin catalyst for static replacement; and the step (d) is as follows: introducing the leachate into the fixed-bed reactor from the washing solution inlet to be in contact with the resin catalyst for leaching, and opening the washing solution outlet of the fixed-bed reactor to drain the leachate, to obtain the pretreated resin catalyst.

3. The pretreatment process for the resin catalyst for synthesizing the bisphenol A according to claim 2, wherein the resin catalyst is acid ion exchange resin, which is one of a gel type or macroporous type, a resin crosslinking degree ranges from 1.0% to 20%, a particle size ranges from 0.4 nm to 5.0 nm, and a water content ranges from 20 wt % to 90 wt %.

4. The pretreatment process for the resin catalyst for synthesizing the bisphenol A according to claim 2, wherein in the step (a), the residual liquid in the resin catalyst is removed through purging of the purging gas, the purging gas enters from an upper portion of a resin catalyst bed, the residual liquid and tail gas are exhausted from a lower portion of the resin catalyst bed, and the purging gas is one or a combination of more of air, ethane, propane, nitrogen, argon, or helium.

5. The pretreatment process for the resin catalyst for synthesizing the bisphenol A according to claim 2, wherein in the step (a), a temperature of the purging gas ranges from 40° C. to 80° C., a flow per minute of the purging gas is 1 to 5 times a filling volume of the resin catalyst, and purging time ranges from 10 minutes to 120 minutes.

6. The pretreatment process for the resin catalyst for synthesizing the bisphenol A according to claim 2, wherein in the step (b), during static replacement, a temperature of a resin catalyst bed ranges from 45° C. to 95° C., a phenol content of the replacement washing solution ranges from 10 wt % to 95 wt %, a temperature of the replacement washing solution ranges from 45° C. to 95° C., a consumption of the replacement washing solution is 0.5 to 3 times a filling volume of the resin catalyst, and standing time ranges from 0.5 hours to 24 hours.

7. The pretreatment process for the resin catalyst for synthesizing the bisphenol A according to claim 2, wherein in the step (b), the purging gas is one or a combination of more of air, ethane, propane, nitrogen, argon, or helium, a temperature of the purging gas ranges from 40° C. to 80° C., a flow per minute of the purging gas is 1 to 5 times a filling volume of the resin catalyst, and purging time ranges from 10 minutes to 120 minutes.

8. The pretreatment process for the resin catalyst for synthesizing the bisphenol A according to claim 2, wherein in the step (c), during static replacement, a temperature of a resin catalyst bed ranges from 45° C. to 95° C., a phenol content of the replacement washing solution ranges from 80 wt % to 99.5 wt %, a temperature of the replacement washing solution ranges from 45° C. to 95° C., a consumption of the replacement washing solution is 0.5 to 3 times a filling volume of the resin catalyst, and standing time ranges from 0.5 hour to 24 hours.

9. The pretreatment process for the resin catalyst for synthesizing the bisphenol A according to claim 2, wherein in the step (d), the leachate is phenol, and a temperature of the leachate ranges from 45° C. to 95° C.

10. The pretreatment process for the resin catalyst for synthesizing the bisphenol A according to claim 2, wherein in the step (d), a flow per hour of the leachate is 0.05 to 0.2 times a filling volume of the resin catalyst, and leaching time ranges from 0.5 hours to 72 hours.

* * * * *